United States Patent [19]

Scheldrup et al.

[11] Patent Number: 5,643,254
[45] Date of Patent: Jul. 1, 1997

[54] ENDOVASCULAR EMBOLIC DEVICE DETACHMENT DETECTION METHOD

[75] Inventors: Ronald W. Scheldrup, Menlo Park; Laurent B. Schaller, Los Altos, both of Calif.

[73] Assignee: Target Therapeutics, Inc., Fremont, Calif.

[21] Appl. No.: 561,169

[22] Filed: Nov. 21, 1995

Related U.S. Application Data

[63] Continuation of Ser. No. 205,512, Mar. 3, 1994, abandoned.

[51] Int. Cl.⁶ .................................................. A61B 17/38
[52] U.S. Cl. ........................... 606/32; 128/630; 606/41; 606/191
[58] Field of Search ............................... 204/114, 129.35, 204/111, 153.1; 205/103; 320/43; 604/286; 606/32, 191, 200

[56] References Cited

U.S. PATENT DOCUMENTS

| | | |
|---|---|---|
| 4,057,063 | 11/1977 | Gieles et al. . |
| 4,416,276 | 11/1983 | Newton et al. . |
| 4,739,768 | 4/1988 | Engelson . |
| 4,884,579 | 12/1989 | Engelson . |
| 4,994,069 | 2/1991 | Ritchart et al. . |
| 5,122,136 | 6/1992 | Guglielmi et al. ................... 606/32 |
| 5,167,658 | 12/1992 | Ensslin . |
| 5,170,802 | 12/1992 | Mehra . |
| 5,190,517 | 3/1993 | Zieve et al. . |
| 5,250,071 | 10/1993 | Palermo . |
| 5,300,068 | 4/1994 | Rosar et al. . |
| 5,304,194 | 4/1994 | Chee et al. . |
| 5,341,807 | 8/1994 | Nardella . |
| 5,354,295 | 10/1994 | Guglielmi et al. ................... 606/32 |
| 5,423,810 | 6/1995 | Goble et al. . |

OTHER PUBLICATIONS

Becker et al., "Long-term occlusion of the porcine cystic duct by means of endoluminal radio-frequency electrocoagulation" *Radiology* (1988) 167:63–68.

Kopecky et al., "Percutaneous transdermal endoureteral radio-frequency electrocautery for occlusion: Case report" *Radiology* (1989) 170:1047–1048.

*Primary Examiner*—Angela D. Sykes
*Assistant Examiner*—Stephen Huang
*Attorney, Agent, or Firm*—Morrison & Foerster, LLP

[57] ABSTRACT

This invention is a method for ensuring for endovascular occlusion through the formation of thrombi in arteries, veins, aneurysms, vascular malformations, and arteriovenous fistulas. In particular, it deals with a method to predictably determine the instant of electrolytic detachment of an embolic device which is introduced to and is intended to remain at the desired thrombus formation site. The invention further includes a method for delivering an embolic device and detecting its electrolytic separation.

21 Claims, 12 Drawing Sheets

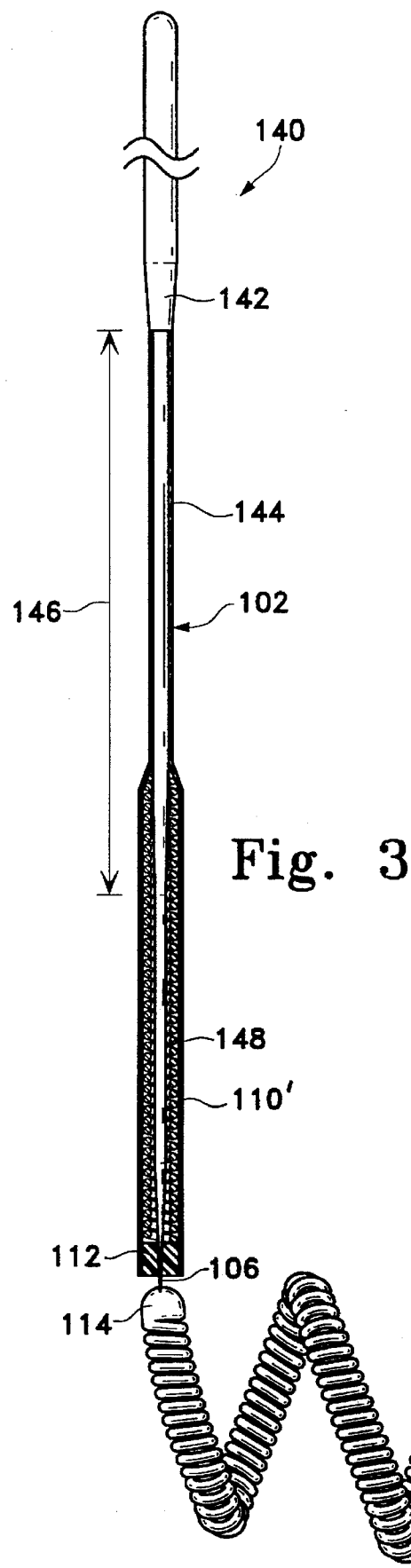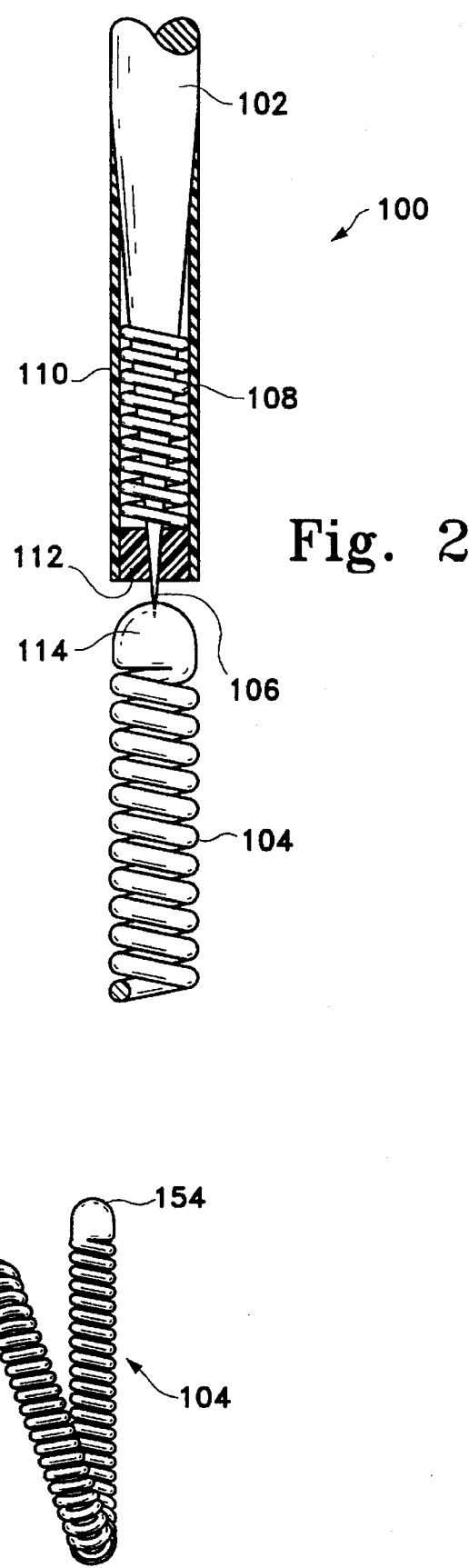

| TABLE I | | DETACHMENT TIME STUDY USING THE ON | | | |
|---|---|---|---|---|---|
| DETACH TIME | | | | | |
| 0:01:44 | | BIN | FREQUENCY | CUMULATIVE% | BIN |
| 0:04:23 | | 0:00:00 | 4 | 13.33% | 0:02:00 |
| 0:02:18 | | 0:01:00 | 6 | 33.33% | 0:01:00 |
| 0:00:37 | | 0:01:30 | 6 | 53.33% | 0:01:30 |
| 0:01:25 | | 0:02:00 | 7 | 76.67% | 0:00:00 |
| 0:02:03 | BIN RANGE | 0:02:30 | 2 | 83.33% | 0:02:30 |
| 0:01:38 | 0:00:00 | 0:03:00 | 0 | 83.33% | 0:04:00 |
| 0:01:39 | 0:01:00 | 0:03:30 | 0 | 83.33% | 0:04:30 |
| 0:01:27 | 0:01:30 | 0:04:00 | 2 | 90.00% | 0:06:00 |
| 0:06:45 | 0:02:00 | 0:04:30 | 2 | 96.67% | 0:03:00 |
| 0:02:16 | 0:02:30 | 0:05:00 | 0 | 96.67% | 0:03:30 |
| 0:02:08 | 0:03:00 | 0:05:30 | 0 | 96.67% | 0:05:00 |
| 0:00:49 | 0:03:30 | 0:06:00 | 1 | 100.00% | 0:05:30 |
| 0:01:04 | 0:04:00 | 0:10:00 | 0 | 100.00% | 0:10:00 |
| 0:00:48 | 0:04:30 | | | | |
| 0:00:59 | 0:05:00 | | | | |
| 0:01:20 | 0:05:30 | | | | |
| 0:01:42 | 0:06:00 | NOTE: | | | |
| 0:01:14 | 0:10:00 | ALL DETACHMENTS WERE WITH 1 mA AT | | | |
| 0:01:40 | | ALL DETACHMENTS WERE DONE IN | | | |
| 0:01:14 | | | | | |
| 0:02:35 | | | | | |
| 0:02:05 | | | | | |
| 0:01:33 | | | | | |
| 0:04:35 | | | | | |
| 0:02:52 | | | | | |
| 0:02:01 | | | | | |
| 0:04:56 | | | | | |
| 0:04:10 | | | | | |
| 0:02:28 | | | | | |

5,643,254

ENDOVASCULAR EMBOLIC DEVICE DETACHMENT DETECTION METHOD

This application is a continuation of application Ser. No. 08/205,512, filed Mar. 3, 1994, now abandoned.

FIELD OF THE INVENTION

This invention is a method for ensuring endovascular occlusion through the formation of mechanical blockage in arteries, veins, aneurysms, vascular malformations, and arteriovenous fistulas. In particular, it deals with a method to indicate predictably, the time of electrolytic separation of an endovascular device which has been introduced to and is intended to remain at the desired thrombus formation site.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms.

Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by reference.

A still further approach, the least invasive, is described in Guglielmi et al. It is the endovascular approach. In this approach, the interior of the aneurysm is entered by use of a catheter such as those shown in Engelson (Catheter Guidewire), U.S. Pat. No. 4,884,575 and also in Engelson (Catheter for Guidewire Tracking), U.S. Pat. No. 4,739,768. These patents describe devices utilizing guidewires and catheters which allow access to an aneurysm from remote portions of the body. Specifically, by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of difficulty in introducing the balloon into the aneurysm sac, the possibility of an aneurysm rupture due to overinflation of the balloon within the aneurysm or due to stress placed on the nonspherically shaped aneurysm by the spherical balloon, and the risk associated with traction produced when detaching the balloon.

A highly desirable embolism-forming device that may be introduced into an aneurysm using endovascular placement procedures, is found in U.S. Pat. No. 4,994,069, to Ritchart et al. The device—typically a platinum/tungsten alloy coil having a very small diameter—may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly hereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136), discussed above.

Guglielmi et al. shows an embolism-forming device and procedure for using that device. Specifically, the Guglielmi device fills a vascular cavity (such as an aneurysm) with an embolic device, typically a platinum coil, that has been endovascularly delivered. The coil is then severed from its insertion tool by the application of a small electric current. Desirably, the insertion device involves a guidewire which is attached at its distal end to the embolic device by a sacrificial joint that is electrolytically dissolvable. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety of ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

U.S. patent application Ser. No. 08/147,529 filed Nov. 3, 1993, describes a variation of the Guglielmi detachable coil using an improved sacrificial link between the guidewire and the coil. The size of the sacrificial link is limited to allow more precise placement of the embolic device and facile, quick detachment. The focussed electrolysis found at the sacrificial site reduces the overall possibility of occurrence of multiple electrolysis sites and liberation of large particles from those sites.

The present invention is a method for detecting the detachment of the endovascular devices described above so that the power supply can be shut down immediately following detachment.

SUMMARY OF THE INVENTION

The present invention is a method for detecting electrolytic separation of an endovascular occlusion device. The method involves monitoring the voltage applied to the endovascular device via a constant current circuit through the human patient, detecting a time-averaged drop in the monitored voltage upon separation of the occlusion device, and shutting down the voltage when the time-averaged voltage drop is greater than about 20%.

In a further aspect, the invention is a method for delivering an endovascular occlusion device. The method involves inserting a guidewire with a distal, discrete, sacrificial line susceptible to electrolytic disintegration in blood. A power supply attached to the guidewire is turned on and delivers a positive electric current. A voltage drop is detectable when the sacrificial link has been severed and the power supply is shut down.

BRIEF DESCRIPTION OF THE DRAWINGS

FIG. 2 shows a sideview of an electrolytically susceptible, sacrificial link between a core wire and an embolic device, the electrolytic separation of which is detectable by the inventive method.

FIG. 3 shows side view of a typical assembly useful in the inventive method.

DESCRIPTION OF THE INVENTION

Figure 1:
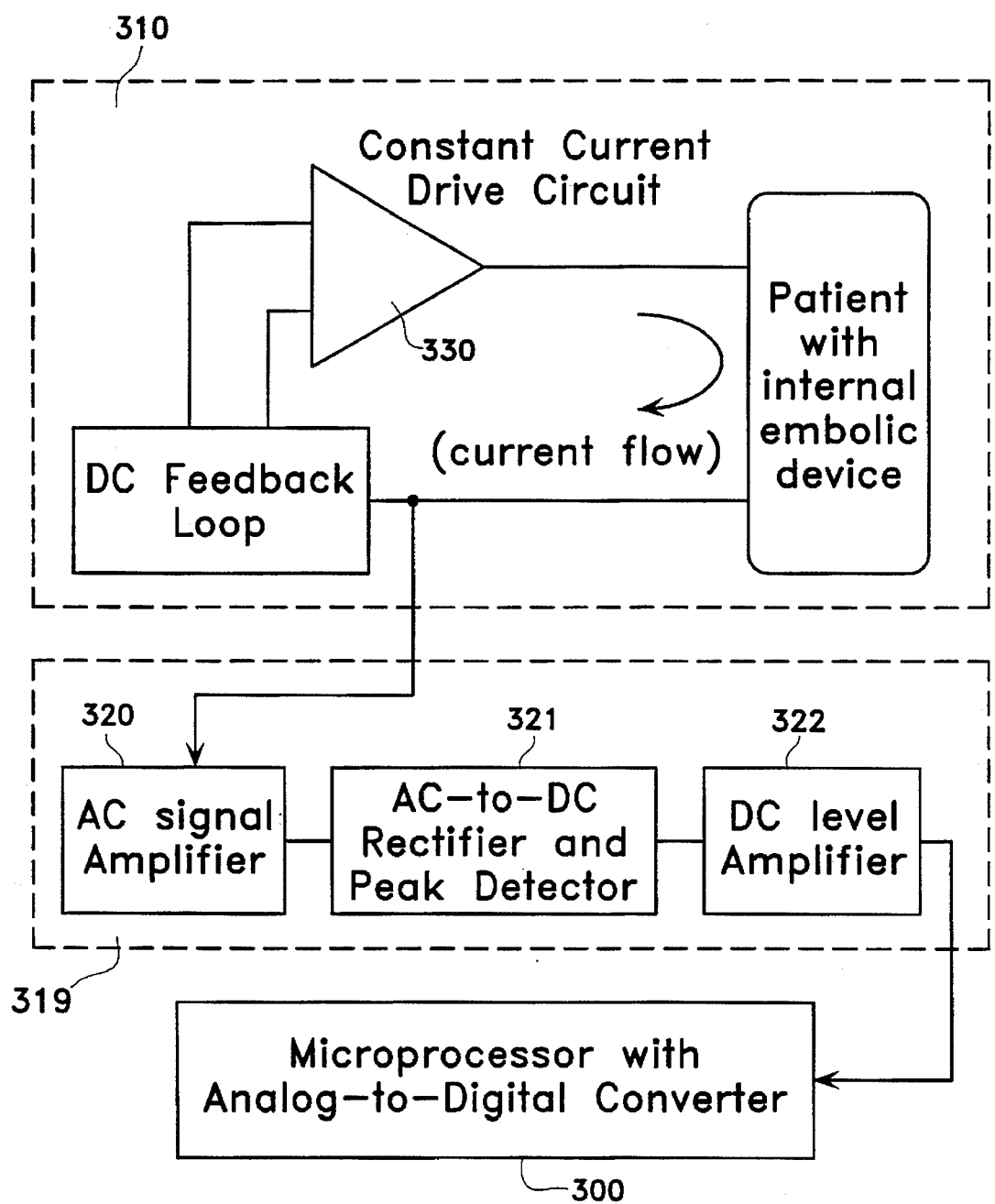
FIG. 1 is a block diagram showing the method for detecting the electrolytic separation of an endovascular occlusion device.

The method of the present invention is shown schematically in FIG. 1. A constant current feedback loop 310 and an embolic device detection circuit (EDDC) 319 are shown. Such circuit provides for accurate detection of the separation of the device from a guidewire. Operation of the circuit is described below. The method for detecting electrolytic separation of the embolic devices may be used with the devices shown in U.S. Pat. No. 5,122,136 to Guglielmi et al., the entirety of which patent is incorporated by reference.

Electrolytic separation of a device from a guidewire may be facilitated by means of the assembly 100 shown in FIG. 2. The assembly 100 is made up generally of a guidewire 102 which tapers at its distal end to a point and is soldered into the proximal end of a vasoocclusive device 104, which in this case is a coil and is of a radiopaque physiologically compatible material such as platinum, tungsten, gold, iridium or alloys of these. All of the guidewire 102 is covered with an insulating material such as Teflon®, polyurethane, polyethylene, polypropylene, or other suitable polymeric material, except the most distal exposed joint or sacrificial link 106. Link 106 is not coated with an electrical insulator and is of a material which is susceptible to electrolytic dissolution in blood such as stainless steel. The core wire 102 is typically stainless steel and may be disposed within a protective catheter not shown. Stainless steel guidewire 102 typically is approximately 10–30 mils. in diameter. Often the guidewire is 50–300 cm. in length, that is to say, from the entry site outside the body to sacrificial link 106.

Sacrificial link 106 is a discrete link. By "discrete" we mean to say preferably that the joint is substantially dissolved upon release of the vasoocclusive device 104. Alternatively, "discrete" may mean that the length of the link 106 is no greater than the diameter of the sacrificial link 106 or that the electrolytic surface present after the vasoocclusive device is released is not substantially greater than would be a circle having the diameter of the sacrificial link 106.

Also shown in FIG. 2 is a coil 108 which is soldered at its proximal end and, typically, is designed to provide some column strength to the guidewire assembly while not detrimentally affecting the flexibility of the tapered portion of the guidewire 102. Obviously, in the area where the support coil 108 is soldered to guidewire 102, the coating on 102 is not present, allowing the solder to adhere to metal surfaces. Further, on the distal tip of core wire 102 may be found a pair of insulators: sleeve 110 and end plug 112 which serve to further remove the stainless steel coil 108 from contact with the blood while the step of electrolytic detachment is carried out. Preferably, the end plug 112 and sleeve 110 are adhesively attached to each other to form an electrically insulating or electrolysis-tight housing about coil 108. The end plug 112 and sleeve 110 form a planar surface in the Figure which is generally planar and perpendicular to the axis of the core wire 102. The shape of the surface is not critical except to the extent it allows reasonably free access of the blood to the sacrificial link 106. Curved, slotted, and other variations of the end surface are also contemplated in this invention.

As noted above, the distal end of the guidewire 102 is inserted into the solder joint 114 forming the proximal end of vasoocclusive device 104.

As will be discussed in more detail below, the discrete sacrificial link 106 is completely or substantially completely dissolved during electrolysis.

Vasoocclusive device 104 is shown to be a coil. It may be a coil or a braid or other vasoocclusive device as is already known. The vasoocclusive device may be covered or connected with fibrous materials tied to the outside of the coil or braided onto the outer cover of the coil as desired. Such fibrous adjuvants may be found in U.S. patent application Ser. No. 07/965,973, to Phelps et al, or in U.S. patent application Ser. No. 07/771,013, entitled "Vasoocclusion Coil with Attached Fibrous Elements", the entirety of which are incorporated by reference.

FIG. 3 shows a typical layout involving the inventive discrete sacrificial link 106 as was generally shown in FIG. 2 above. In FIG. 3, a somewhat conventional Teflon® laminated or similarly insulated stainless steel guidewire 102 may be placed within a protective catheter. As was noted above, stainless steel guidewire 102 may have a diameter of approximately 10–30 mils. In the embodiment illustrated in FIG. 3, guidewire assembly 140 is shown as including guidewire 102, which is tapered at its distal end to form a conical section 142 which joins a further section 144 that extends along a length of the guidewire designated with reference numeral 146. Section 144 then gradually narrows down to a thinner section 148. The guidewire assembly 140, as noted above, may be placed within a catheter body and is typically 50–200 cm. in length down to sacrificial link 106.

As was shown in FIG. 2, the distal section of guidewire assembly 140 has an outer Teflon® sleeve 110' (or sleeve of other appropriate insulating material) which is shown somewhat longer than the sleeve 110 in FIG. 2. Furthermore, it has an end plug 112 to permit isolation of the guidewire electrically from the blood except at sacrificial discrete link 106. The proximal end of vasoocclusive device 104 is typically a soldered tip or a joint 114. Preferably, vasoocclusive device 104, when a coil, forms a secondary loop after it emanates from the end of the catheter. The distal end of vasoocclusive device 104 may also have an end plug or tip 154 to prevent punctures of the aneurysm when introduced into the aneurysm sac.

Coil or vasoocclusive device 104 may be pre-biased to form a cylinder or conical envelope. However, the vasoocclusive device 104 is extremely soft and its overall shape is easily deformed. When inserted within the catheter (not shown), the vasoocclusive device 104 is easily straightened to lie axially within the catheter. Once ejected from the tip of the catheter, vasoocclusive device 104 may form a shape shown in FIG. 3 or may be loosely deformed to conform to the interior shape of the aneurysm.

Figure 4:
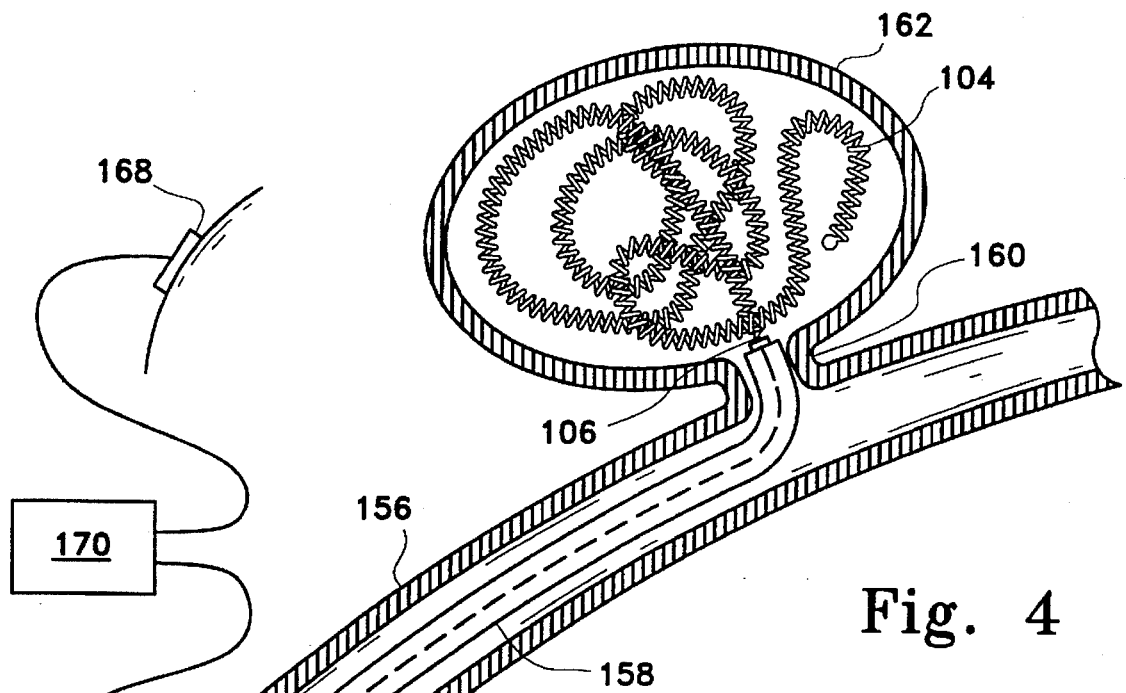
FIGS. 4 and 5 schematically depict the method for deploying a vasoocclusive device using the inventive method.

FIG. 4 shows the placement of the inventive devices described above within a vessel 156 with the tip of catheter 158 placed near neck 160 of aneurysm 162. A vasoocclusive device, such as device 104 (FIG. 4) is fed into aneurysm 162 at least until sacrificial link 106 is exposed beyond the distal tip of the catheter 158. A positive electric current of approximately 0.01–10 milliamps, preferably about 1 milliamp, at 0.1–6 volts, is applied to guidewire 102 to form a thrombus within aneurysm 162. The negative pole 168 of power supply 170 is typically placed in electrical contact with the skin.

After the thrombus has been formed and the aneurysm occluded, vasoocclusive device 104 is detached from guidewire 102 by electrolytic disintegration of sacrificial link 106.

Figure 5:
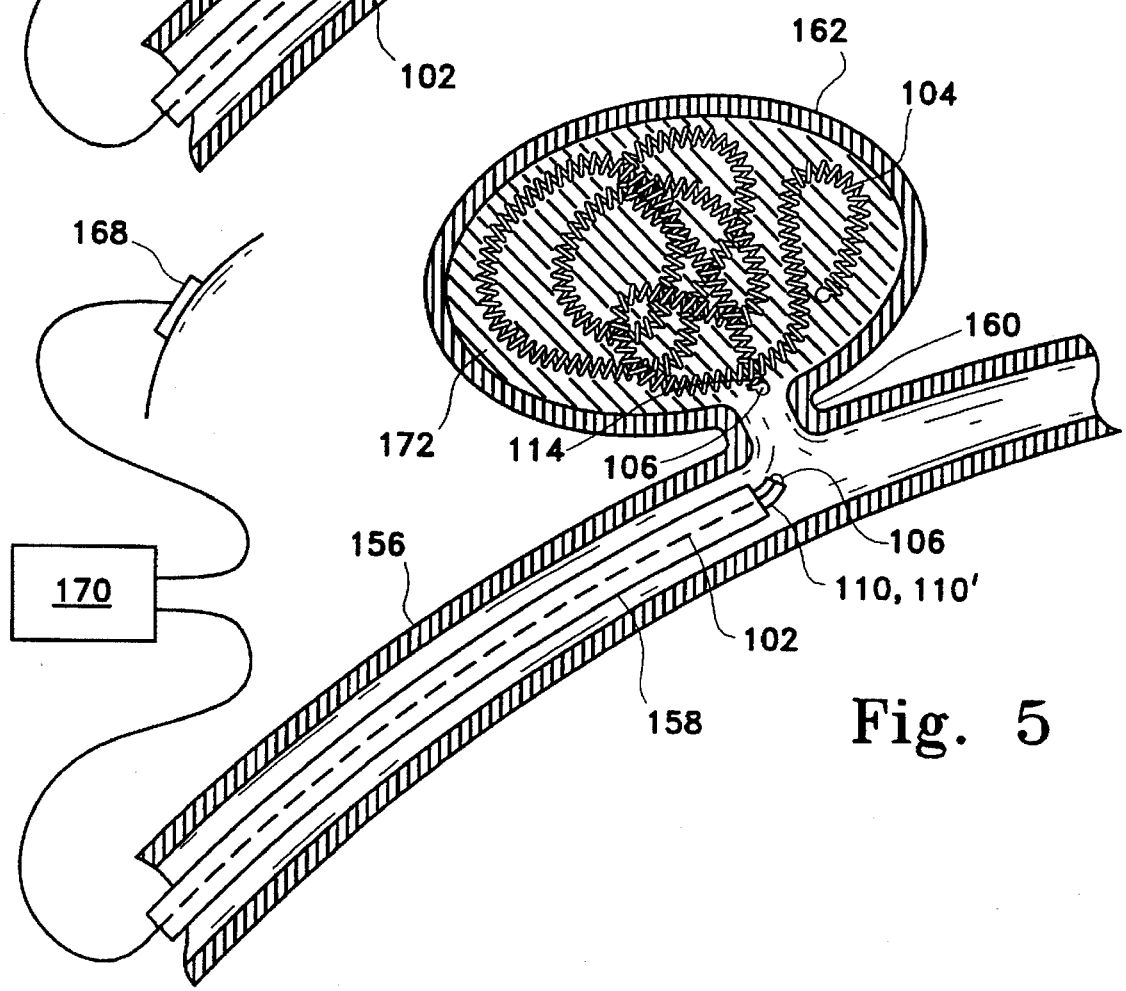

After sacrificial link 106 is completely dissolved by electrolytic action, typically within 3–10 minutes, the guidewire 102, catheter 158, are removed from vessel 156, leaving aneurysm 162 occluded as shown in FIG. 5.

The process is typically practiced under fluoroscopic control with local anesthesia. A transfemoral catheter is utilized to treat a cerebral aneurysm and is usually introduced at the groin. The physician guides the distal tip of the catheter to the target site. The embolic device is then inserted into the catheter. Using a fluoroscope, the physician guides the device to the desired position before separation is initiated. When the vasoocclusive device 104 is platinum, it is not effected by electrolysis. When the guidewire and pertinent portions of the supporting coils at the distal tip of the guidewire are adequately coated with insulating coverings, only the exposed portion at the sacrificial link 106 is effected by the electrolysis.

The positive terminal of the power supply is attached to the proximal end of the guidewire. A needle with a ground wire attached is connected between the negative terminal of the power supply and the opposite thigh of the patient. Alternatively, a ground wire with a skin patch located behind the shoulder of the patient may be used.

Figure 6:
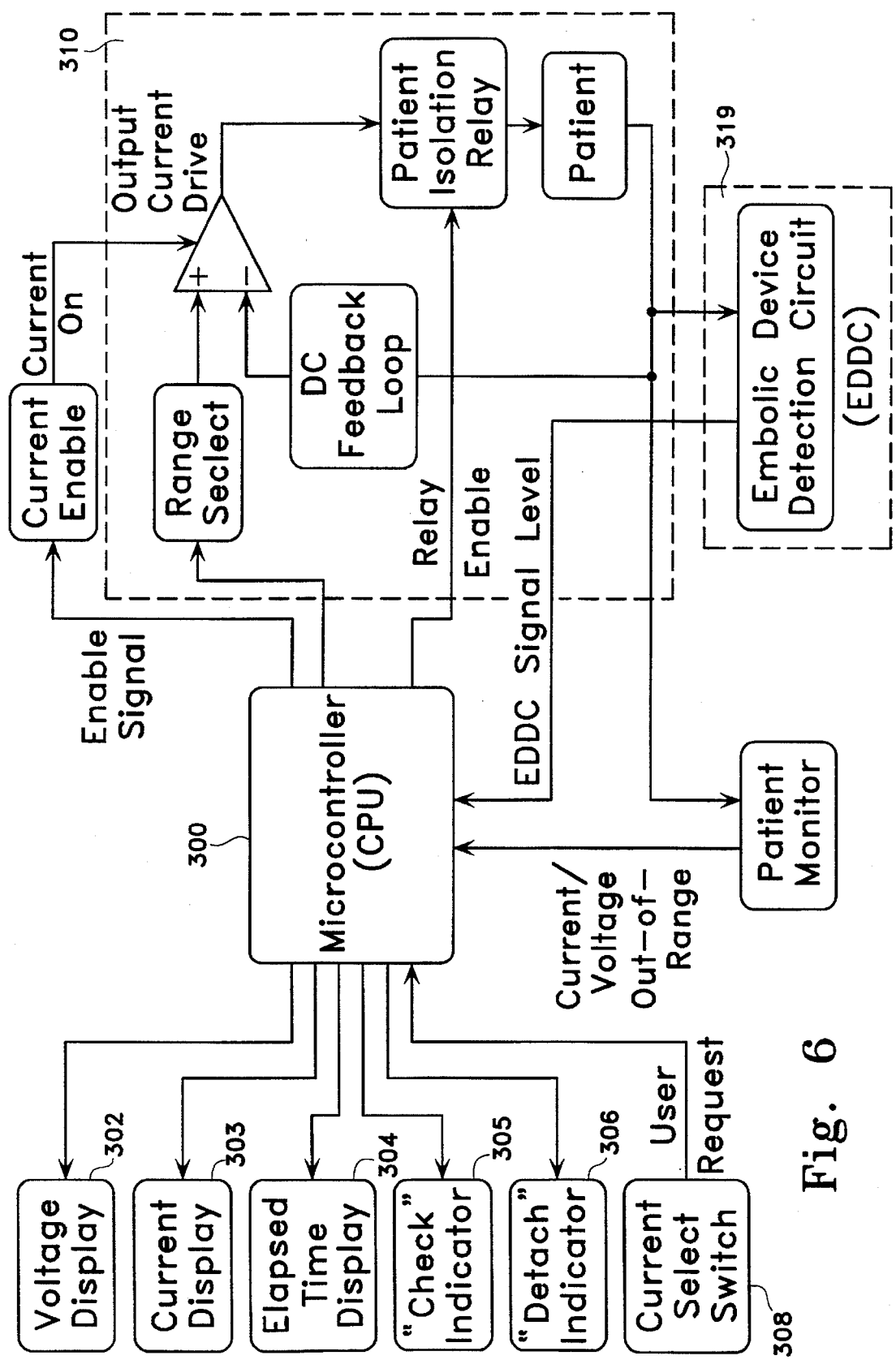
FIG. 6 is a block diagram showing the system architecture for delivery of the embolic device.

Power is supplied via terminals marked plus (+) and minus (−) on microcontroller 300 as shown in FIG. 6. A DC current of between about 0.1 and 10 milliamps at 0.1 to 6 volts is sent through the embolic device and patient. The voltage display 302 is a three digit red LED readout that displays the voltage required to maintain the current flowing through the coil and the patient. The fixed-decimal display shows voltages from 0.00 to 9.99 volts DC. In Pause Mode, that is, when electrolytic separation has occurred, the display shows the voltage immediately prior to coil detachment. The current display 303 is a three digit red LED readout that displays the actual current flowing through the coil and the patient. The fixed-decimal display shows current from 0.00 to 1.25 mA DC. In addition, the display briefly flashes the new current setting when the front panel current select switch is pressed or when power-up occurs, and then returns to the continuous display of actual current. In Pause Mode, the display shows the current immediately prior to coil detachment. The current may be changed by the physician at any time. In Normal Mode, the current-select switch 308 is used to change the current setting. When the power supply is turned on, the current is automatically set to 1.00 milliamps. Pressing the current-select switch one time changes the setting to 0.50 milliamps, pressing it a second time changes it to 0.75 milliamps and pressing it a third time returns the setting to 1.00 milliamps. Each time the switch is pressed, the current display 303 briefly flashes the new current setting. In Pause Mode, pressing the current-select switch 308 will resume Normal Mode. The current and voltage displays 303 and 302 resume the real-time display of these parameters and the elapsed time display 304 resumes counting from where it was paused.

The current flowing through the embolic device initiates electrolysis near the junction between the embolic device, in this case the platinum coil and the guidewire. Over a period of several minutes, the electrolysis dissolves the exposed steel and the embolic device detaches completely from the guidewire. The elapsed time display 304, a four digit red LED readout, displays the elapsed time in minutes and seconds from the start of the procedure. The flashing colon display shows elapsed time from 00:00 to 59:59. The check indicator 305, a yellow LED indicator turns on when the microprocessor and EDDC electronics determine that coil detachment has occurred, and indicates that the power supply has entered Pause Mode. The detach indicator 306 flashes when the power supply is in Pause Mode after detecting a coil detachment. In each case, the physician is instructed to check detachment using fluoroscopy. In Pause Mode, the display shows the time required to detach the coil.

The CPU 300 in this case is a Motorola MC68HC811E2FN single-chip microcontroller with 2048 bytes of EEPROM, 256 bytes of RAM, an 8 channel 8-bit A/D converter, and three 8-bit I/O port controls and monitors vital functions of the power supply. Other similar microprocessors may be useful in the inventive method as well. The CPU 300 is responsible for monitoring input battery voltage, output (coil) voltage and current, elapsed time and requests for changing the coil current. The CPU is outside the critical path of the current control loop, which is implemented in hardware. The CPU manages the LED displays, status indicators and beeper, runs self-diagnostic tests at power-on, issues current setting changes and the fail-safe current enable signal, monitors the EDDC signal to determine when coil detachment has occurred, monitors the current-select switch, and communicates with a PC during programming.

The constant current feedback loop 310 monitors an error-correction voltage required to maintain the steady current through the patient. The embolic device detection circuit 319, a feedback loop, identifies separation of the embolic device, as reflected in changes in the amplitude of the error correction voltage from the constant-current source. The error correction voltage signal is amplified 320 and rectified 321 by the embolic device detection circuit (EDDC) and is then sent to the CPU for analysis.

Figure 7:
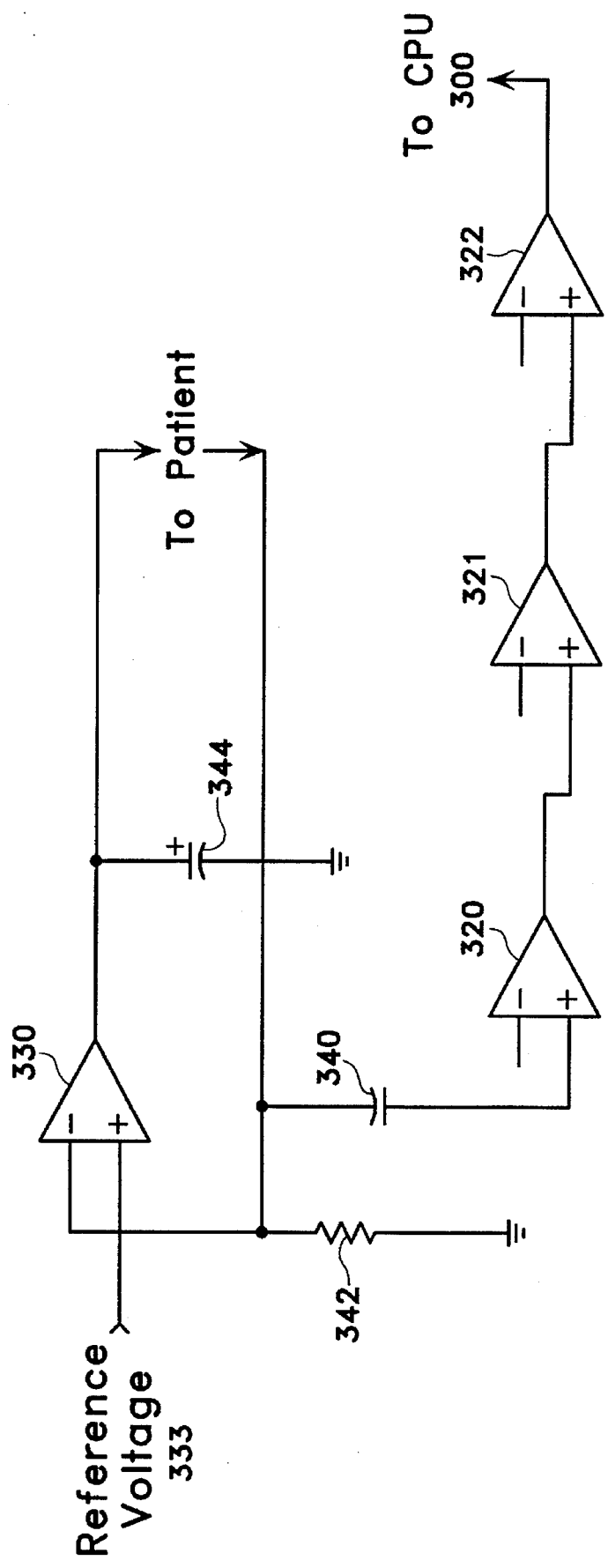
FIG. 7 is a circuit diagram showing the system electronics for monitoring delivery of the embolic device.

The construction of the EDDC is shown in FIG. 7. It is desired to maintain the output of amplifier 330 at a constant current. Amplifier 330 is preferably a National Semiconductor LMC660CN. This device was chosen because of its ability to operate on a single (positive) power supply and because it has a high voltage gain of 126 decibels (dB) and a Gain Bandwidth Product of 1.4 Megahertz (MHz). When the constant current amplifier 330 has achieved equilibrium—when the output current exactly matches the setpoint present at the non-inverting input terminal—the amplifier will oscillate at approximately 20 to 24 kilohertz (kHz) at an amplitude of several hundred millivolts due to a lagging error correction signal (out-of-phase feedback). Thus, the amplifier delivers constant DC current with AC superposition. The amplitude of this signal is dependent on the band-width characteristics of the constant current amplifier and the impedance of the steel and the platinum coils and of the patient's body. Capacitor 344, a 4.7 microfarad tantalum capacitor, is used to reduce the amplitude of the self-oscillation voltage to between about 40 to 60 millivolts AC while maintaining a rapid DC response.

Accordingly, a reference voltage 333 is held constant, in this case from 0.166 to 0.332 volts. These voltages represent a constant current output of between 0.5 and 1 milliamp. Resistor 342, with a resistance in this instance of 332 ohms, is connected between the inverting input terminal of amplifier 330 and ground and ensures the maintenance of the constant current flow from amplifier 330.

The constant current flowing out of amplifier 330 flows through the patient's body and the embolic device as described previously. The resistance of the patient's body is often in the range of 1000 to 4000 ohms, with 3300 ohms being typical.

In the EDDC, the AC feedback signal generated when the current flows through the patient's body is selectively passed through capacitor 340, in this case, a 0.1 microfarad monolithic capacitor. The AC signal is then amplified in the AC signal amplifier 320, rectified in the AC to DC rectifier 321 and the resulting DC signal is further amplified in DC amplifier 322. The amplified DC signal, the level of which is representative of the amplitude of the error correction voltage of constant current amplifier 330 is then sent to the microprocessor (CPU) 300 for analysis as described below.

By monitoring the level of the amplified DC signal every 10 to 250 milliseconds, preferably every 50 to 200 milliseconds, and constantly averaging the signal every 5 to 50 samples, preferably every 10–20 samples or every 0.5–10 seconds, preferably every 2–6 seconds, the CPU can accurately determine the instant the embolic device detaches. When the embolic device detaches, constant current amplifier 330 is no longer in equilibrium and instantly reacts to the change in impedance. During the next several dozen milliseconds, amplifier 330 makes large corrections to the DC output voltage to maintain the set current, which disrupts the stable self-oscillation feedback. During this period the amplified EDDC signal will show a sudden voltage drop of greater than 10%, preferably a drop of greater than 20% of the average level for the procedure. This sudden voltage drop reliably detects the dissolution of the junction between the embolic device and the guidewire. Previous methods relied simply on the increase in impedance upon coil detachment. When the sudden voltage drop is detected, the microprocessor immediately halts current flow, energizes the patient isolation relay, freezes the voltage, current and time displays, and emits five beeps to indicate to the physician that coil detachment has occurred. When the power supply is in this "Pause Mode" no further electrolysis can occur.

Using fluoroscopy, the physician can verify that detachment has occurred. If detachment is incomplete and further electrolysis is necessary, the procedure can be resumed by pressing the current-select switch on the front panel. If detachment is verified, the physician can turn off the power supply and withdraw the guidewire. If necessary, another coil can be placed at the site and the power supply started again. If no action is taken, the power supply will automatically turn itself off after 15 minutes.

The following Example is intended to illustrate but not to limit the invention in any manner.

EXAMPLE

Detachment time studies were run in a preclinical setting using the Guglielmi Detachable Coil (GDC) as described in Guglielmi et al. with the inventive detection system (see Table I). Thirty pigs were anesthetized and catheterized such that a platinum coil was positioned inside the internal carotid artery. The time of coil detachment was determined using the EDDC. For 28 of the samples, at time 0, the 1 milliamp of power was supplied, for one sample 0.5 milliamps of power was supplied and for one sample 0.75 milliamps of power was supplied. The constant current circuit was monitored as was the embolic device detection circuit. As reflected in Table I, detachment occurred in all cases within 6 minutes of supplying power supply and the majority of detachments occurred within 2 minutes.

The inventive electrolytic separation detection method has been described with reference to a platinum coil and stainless steel sacrificial link for the purposes of illustration of a particular embodiment of the invention and should not be taken as limiting the invention. Many alterations and modifications may be made by those having ordinary skill in the art without departing from the spirit and scope of the invention as defined by the following claims.

We claim as our invention:

1. A method for detecting electrolytic separation of an occlusion device comprising the steps of:
   (a) providing a delivery member and an occlusion device coupled to the delivery member via a linking member;
   (b) delivering the occlusion device to a desired site in a mammal via the delivery member;
   (c) supplying DC power with a superposed AC signal to the linking member; and
   (d) monitoring the superposed AC signal to detect a change in said signal.

2. The method of claim 1 wherein step (a) includes selecting the occlusion device to be a vasoocclusive coil.

3. The method of claim 2 wherein step (a) includes selecting the vasoocclusive coil to comprise a radiopaque physiologically compatible material.

4. The method of claim 3 wherein step (a) includes selecting the material from the group consisting of platinum, tungsten, gold, iridium and alloys thereof.

5. The method of claim 4 wherein steps (a) includes selecting the material to be platinum.

6. The method of claim 1 wherein step (c) includes selecting the DC power to provide a voltage in a range of about 0.1 to 6 volts.

7. The method of claim 1 wherein step (c) includes selecting the DC power to provide constant current in a range of about 0.1 to 10 milliamps.

8. The method of claim 1 wherein step (a) includes selecting the linking member to be stainless steel.

9. The method of claim 1 further including the step of interrupting the DC power supply to the linking member in response to detecting a sudden change in the superposed AC signal.

10. The method of claim 1 wherein the AC signal includes a voltage amplitude and step (d) comprises monitoring the voltage amplitude of the AC signal and further including the steps of averaging the monitored voltage amplitude over time to obtain an average monitored value and interrupting the DC power supply to the linking member when at least about a 20% change from the average monitored value is detected.

11. The method of claim 1 wherein step (c) includes providing a constant DC current with AC superposition to the linking member.

12. The method of claim 1 wherein step (a) includes selecting the linking member to have a conductivity that differs from that of the occlusion device.

13. The method of claim 1 wherein step (a) includes providing a linking member comprising stainless steel and the occlusion device to comprise a material selected from the group consisting of platinum, tungsten, gold, iridium and alloys thereof.

14. The method of claim 1 wherein step (a) includes selecting the delivery member to be a guidewire.

15. A method for detecting electrolytic separation of an occlusion device comprising the steps of:
(a) delivering an occlusion device, which is coupled to a delivery member via a linking member, to a desired site in a mammal via the delivery member;
(b) forming a circuit path including the linking member and occlusion device;
(c) supplying DC power with a superposed AC signal to said circuit path; and
(d) monitoring the AC impedance of said circuit path to detect a change in said impedance.

16. The method of claim 15 wherein said monitoring step includes monitoring the AC impedance of said circuit path to detect a change in said impedance indicative of separation between the occlusion device and linking member.

17. The method of claim 15 wherein the AC signal includes a voltage amplitude and step (d) comprises monitoring the voltage amplitude of the AC signal and further including the steps of averaging the monitored voltage amplitude over time to obtain an average monitored value and interrupting the DC power supply to the linking member when at least about a 20% change from the average monitored value is detected.

18. The method of claim 15 wherein the AC signal includes a voltage amplitude and said step (d) comprises monitoring the voltage amplitude of the AC signal and further including the step of interrupting the DC power supply to the linking member in response to detecting a predetermined change in the AC signal amplitude.

19. A method for detecting electrolytic separation of an occlusion device comprising the steps of:
(a) delivering an occlusion device, which is coupled to a delivery member via a linking member, to a desired site in a mammal via the delivery member;
(b) supplying DC power with a superposed AC signal to the linking member; and
(c) monitoring the superposed AC signal to detect a change therein indicative of separation between the occlusion device and delivery member.

20. The method of claim 19 wherein the AC signal includes a voltage amplitude and step (c) comprises monitoring the voltage amplitude of the AC signal and further including the step of interrupting the DC power supply to the linking member in response to detecting a predetermined change in the AC signal amplitude.

21. The method of claim 19 wherein the AC signal includes a voltage amplitude and step (d) comprises monitoring the voltage amplitude of the AC signal and further including the steps of averaging the monitored voltage amplitude over time to obtain an average monitored value and interrupting the DC power supply to the linking member when at least about a 20% change from the average monitored value is detected.

\* \* \* \* \*

UNITED STATES PATENT AND TRADEMARK OFFICE

CERTIFICATE OF CORRECTION

Page 1 of 3

PATENT NO. : 5,643,254

DATED: July 1, 1997

INVENTOR(S) : Ronald W. Scheldrup et al.

It is certified that error appears in the above-identified patent and that said Letters Patent is hereby corrected as shown below:

In column 8, line 54 (claim 5), replace "steps" with --step--.

Figure 8A:
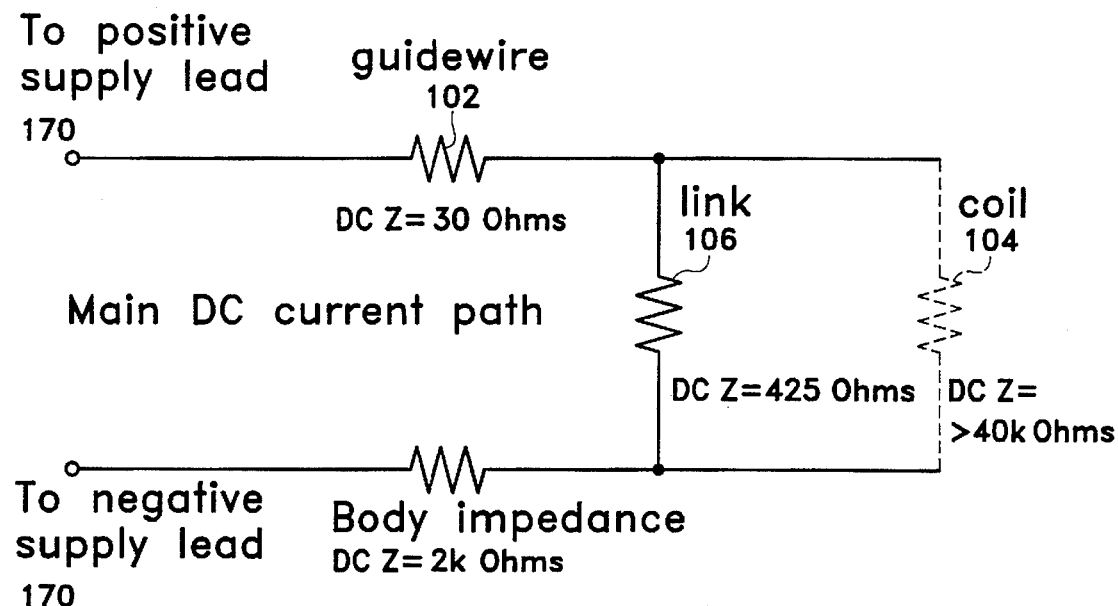
FIGS. 8A and 8B show a table of data from a detachment time study using the ON PCDC power supply.
Figure 8B:
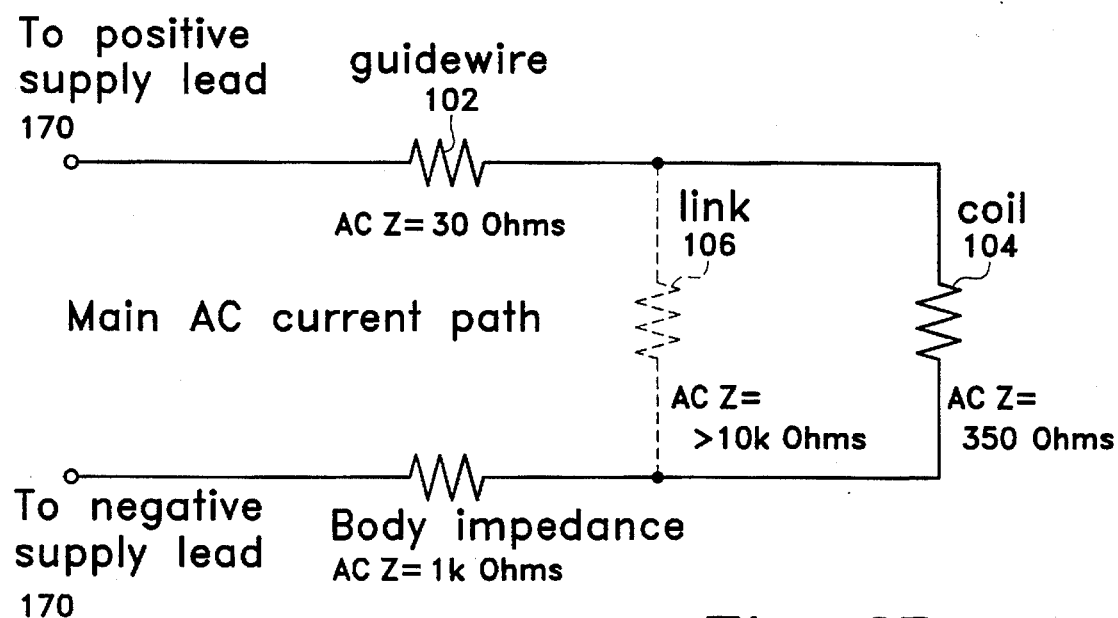
Figure 9:
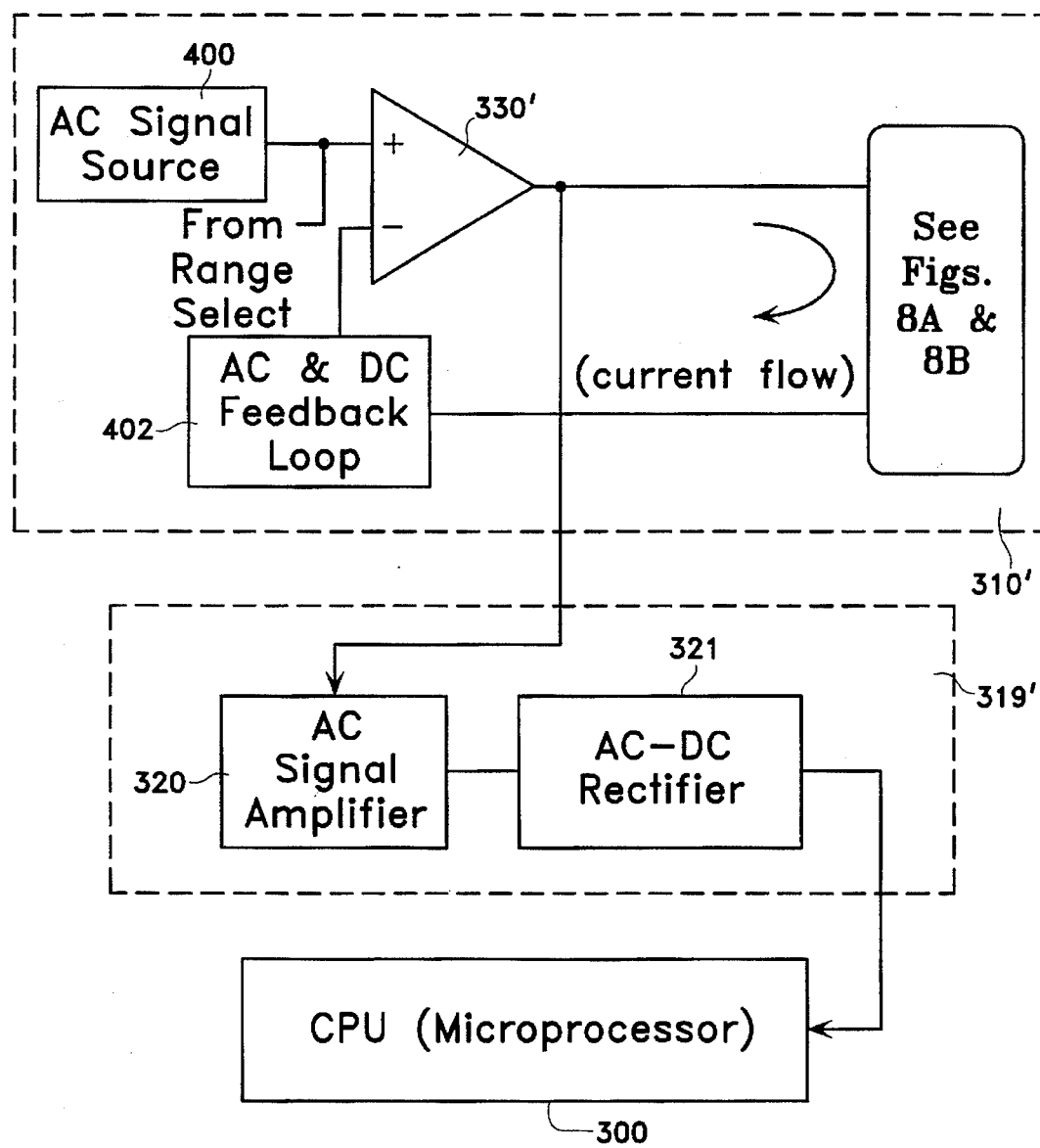
Figure 10:
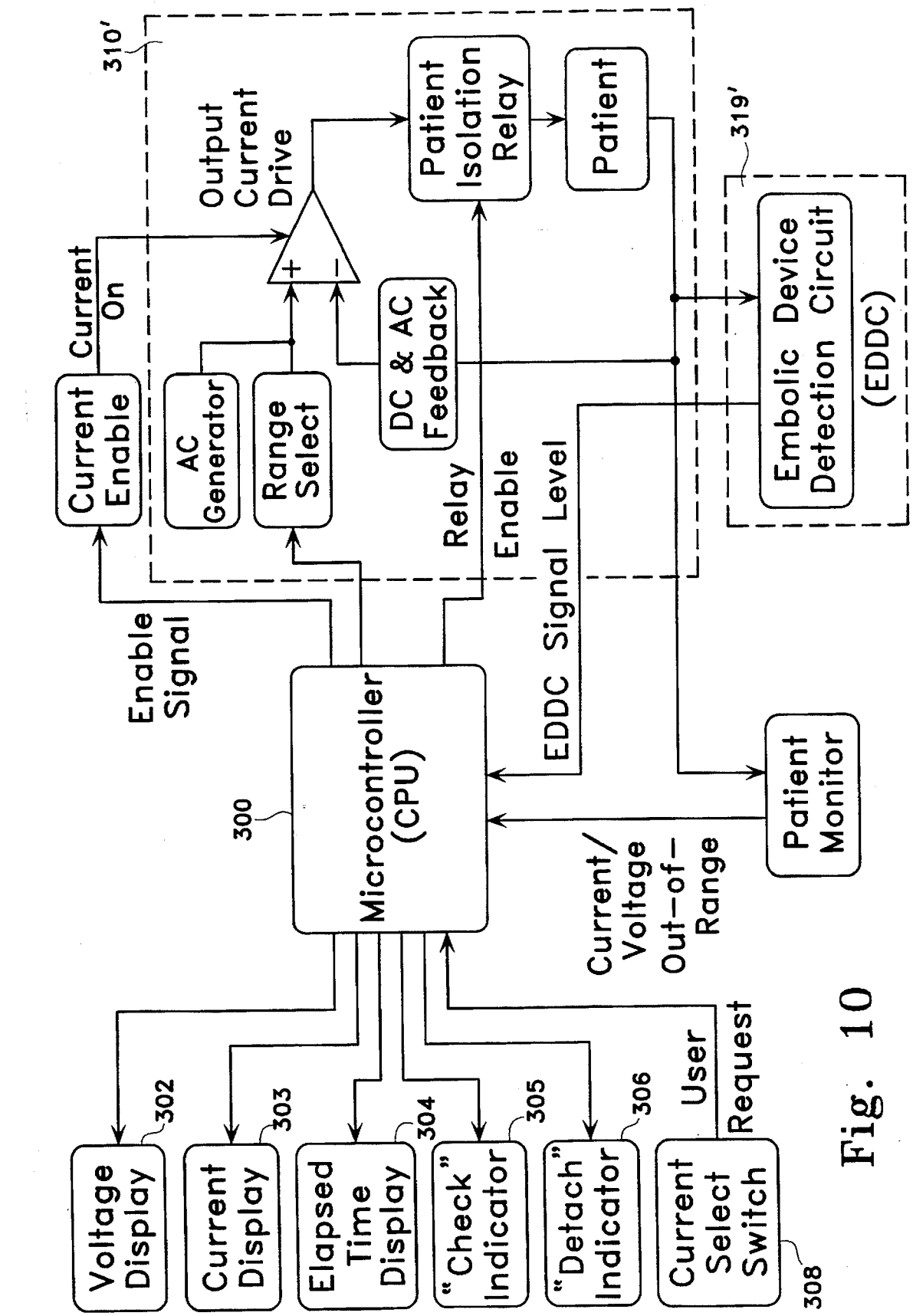
Figure 11:
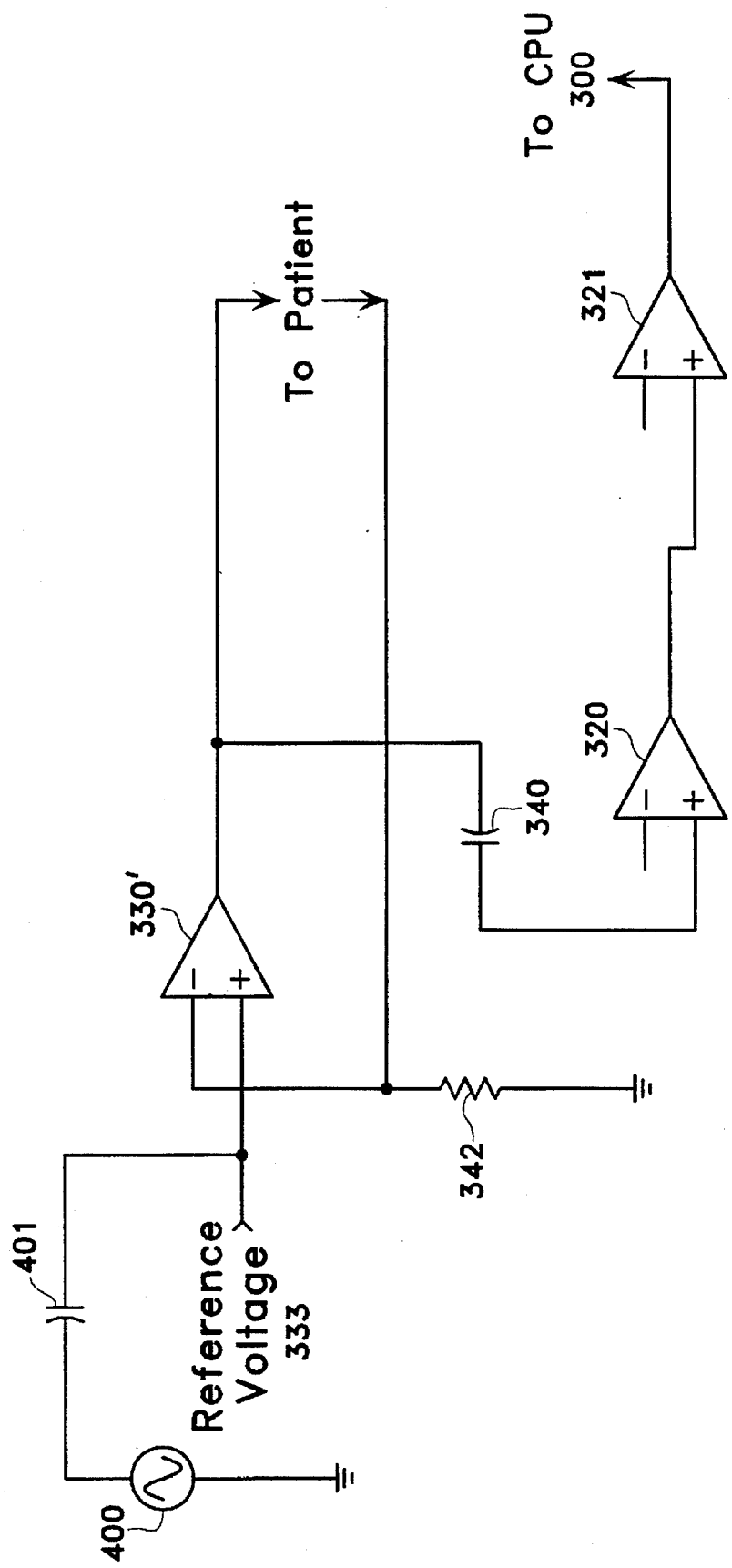
Figure 12:
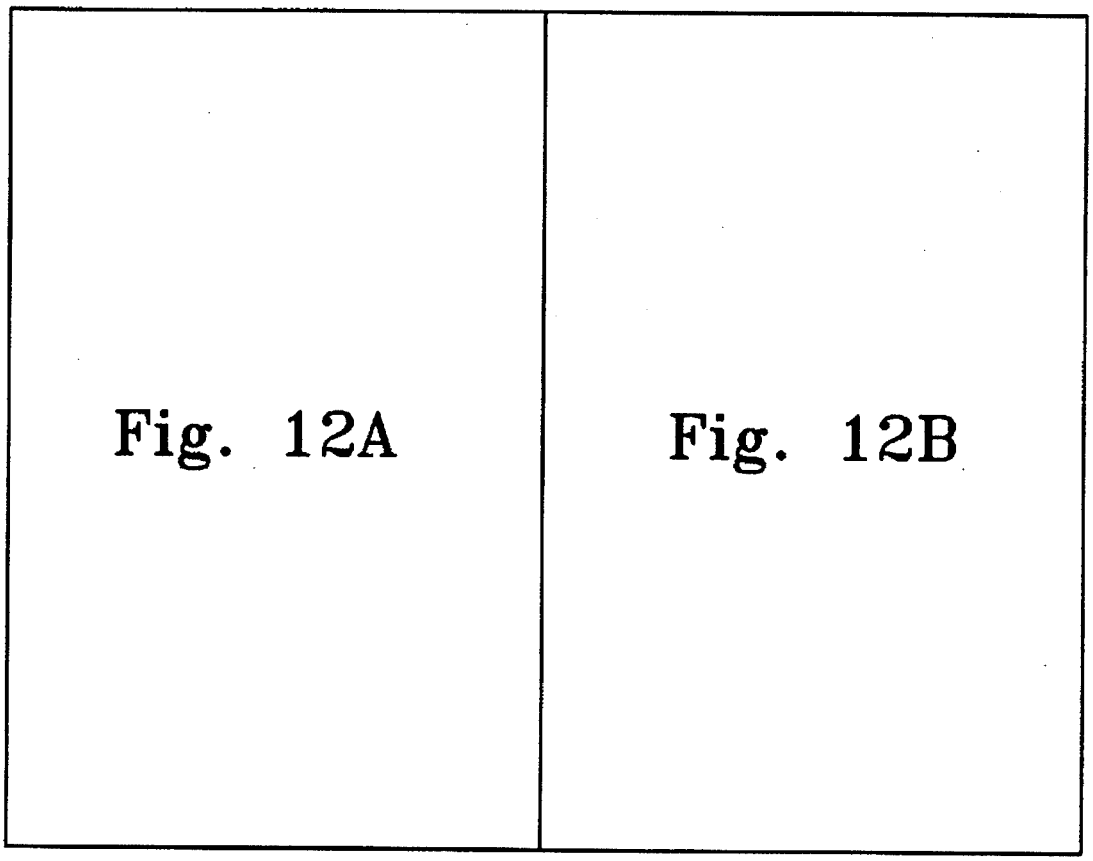
Figure 12A:
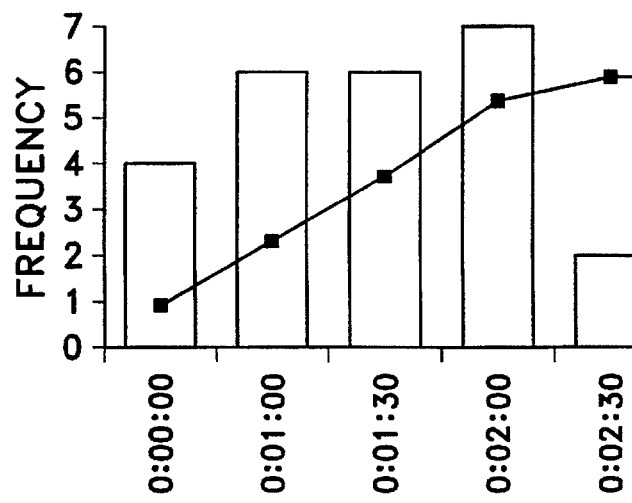
Figure 12B:
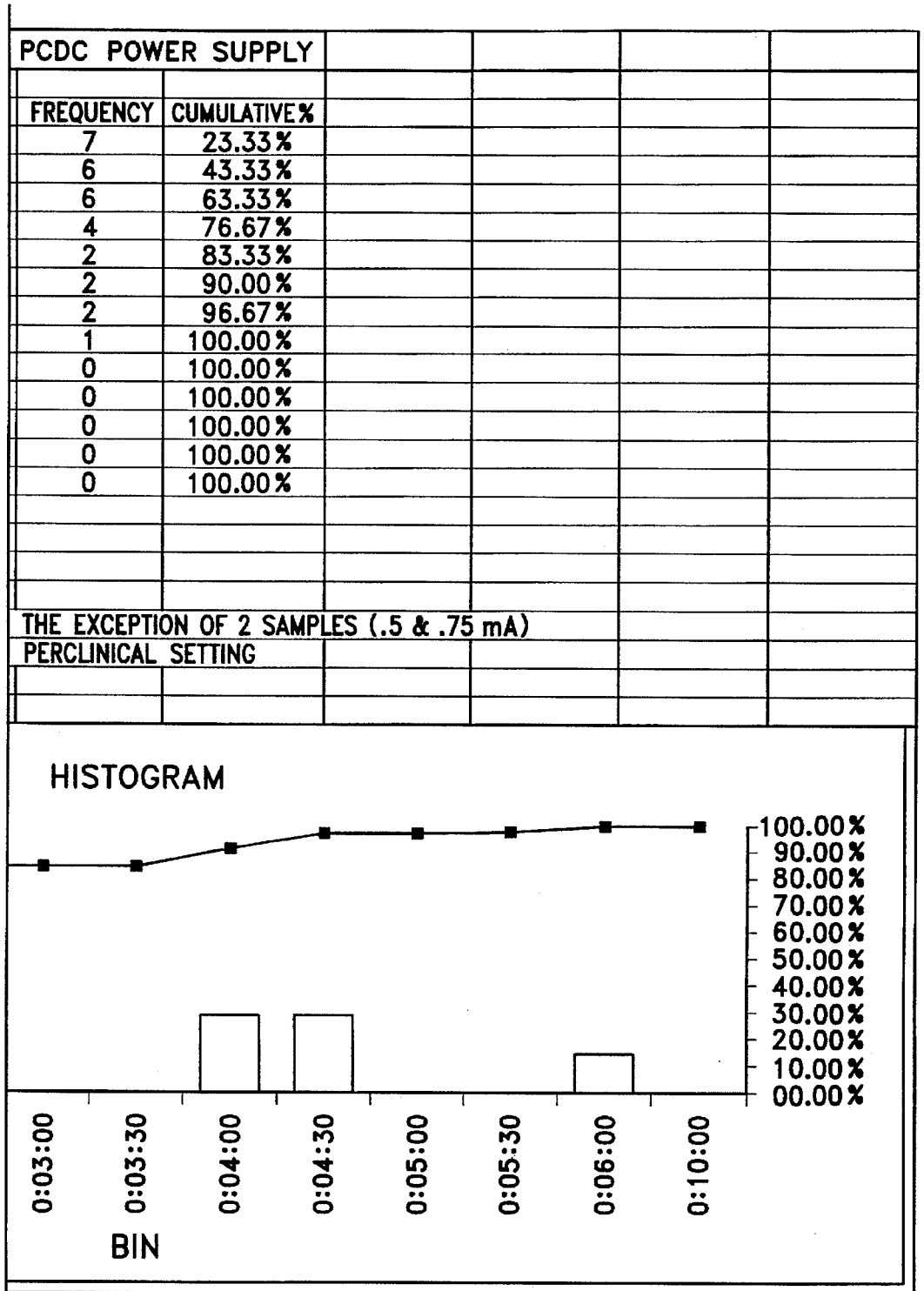
Figure 8B:
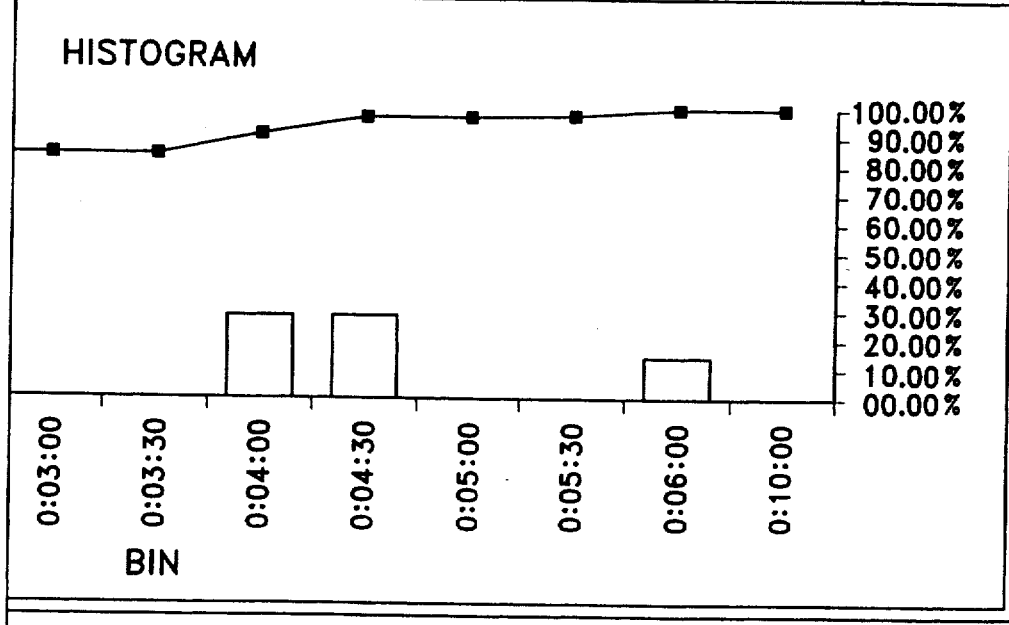

In the drawings:
Please replace Figures 8A-12B with new Figures 8A and 8B provided herewith.

Signed and Sealed this

Thirtieth Day of December, 1997

*Attest:*

BRUCE LEHMAN

*Attesting Officer*    *Commissioner of Patents and Trademarks*

| TABLE I | | DETACHMENT TIME STUDY USING THE ON | | | |
|---|---|---|---|---|---|
| DETACH TIME | | | | | |
| 0:01:44 | | BIN | FREQUENCY | CUMULATIVE% | BIN |
| 0:04:23 | | 0:00:00 | 4 | 13.33% | 0:02:00 |
| 0:02:18 | | 0:01:00 | 6 | 33.33% | 0:01:00 |
| 0:00:37 | | 0:01:30 | 6 | 53.33% | 0:01:30 |
| 0:01:25 | | 0:02:00 | 7 | 76.67% | 0:00:00 |
| 0:02:03 | BIN RANGE | 0:02:30 | 2 | 83.33% | 0:02:30 |
| 0:01:38 | 0:00:00 | 0:03:00 | 0 | 83.33% | 0:04:00 |
| 0:01:39 | 0:01:00 | 0:03:30 | 0 | 83.33% | 0:04:30 |
| 0:01:27 | 0:01:30 | 0:04:00 | 2 | 90.00% | 0:06:00 |
| 0:06:45 | 0:02:00 | 0:04:30 | 2 | 96.67% | 0:03:00 |
| 0:02:16 | 0:02:30 | 0:05:00 | 0 | 96.67% | 0:03:30 |
| 0:02:08 | 0:03:00 | 0:05:30 | 0 | 96.67% | 0:05:00 |
| 0:00:49 | 0:03:30 | 0:06:00 | 1 | 100.00% | 0:05:30 |
| 0:01:04 | 0:04:00 | 0:10:00 | 0 | 100.00% | 0:10:00 |
| 0:00:48 | 0:04:30 | | | | |
| 0:00:59 | 0:05:00 | | | | |
| 0:01:20 | 0:05:30 | | | | |
| 0:01:42 | 0:06:00 | NOTE: | | | |
| 0:01:14 | 0:10:00 | ALL DETACHMENTS WERE WITH 1 mA AT | | | |
| 0:01:40 | | ALL DETACHMENTS WERE DONE IN | | | |
| 0:01:14 | | | | | |
| 0:02:35 | | | | | |
| 0:02:05 | | | | | |
| 0:01:33 | | | | | |
| 0:04:35 | | | | | |
| 0:02:52 | | | | | |
| 0:02:01 | | | | | |
| 0:04:56 | | | | | |
| 0:04:10 | | | | | |
| 0:02:28 | | | | | |

Fig. 8A